United States Patent [19]

Zaiger

[11] Plant 4,163

[45] Dec. 13, 1977

[54] PEACH TREE

[76] Inventor: Chris Floyd Zaiger, 537 Rosemore Ave., Modesto, Calif. 95351

[21] Appl. No.: 731,446

[22] Filed: Oct. 12, 1976

[51] Int. Cl.[2] ..... A01H 5/03
[52] U.S. Cl. ..... Plt./43
[58] Field of Search ..... Plt./43

*Primary Examiner*—Robert E. Bagwill

[57] ABSTRACT

This invention relates to a new and distinct variety of peach tree characterized by its dwarf size, heavy attractive foliage, large showy pink flowers and a regular bearer of medium to large, semi-freestone peaches of good eating quality. The variety being adapted for growing as an ornamental tree and also for the production of fruit for the home and local market.

1 Drawing Figure

ORIGIN OF VARIETY

The new and distinct variety of dwarf peach tree was originated by me in my experimental orchard located near Modesto, Calif. It was selected from a group of second generation seedlings obtained by selfing a selected seedling of a cross between Royal Gold peach (U.S. Plant Pat. No. 2,663) and a seedling of Flory dwarf peach (unpatented). These seedlings were planted and grown under careful observation by me, one such seedling which is the present variety, having been especially desirable with respect to its fruit and the dwarf size of the tree.

ASEXUAL REPRODUCTION OF THE VARIETY

Asexual reproduction was accomplished by me in my experimental orchard located near Modesto, Calif., by budding and grafting and such reproduction have run true in all respects.

SUMMARY OF THE VARIETY

The present variety of peach tree is of dwarf size, having close leaf nodes, attractive foliage, large showy flowers, spreading growth habit, and is a regular and productive bearer of medium to large, yellow flesh, semi-freestone fruit of good eating quality. The present dwarf variety when compared to the Flory dwarf peach is larger in size, more even ripening, firmer, and superior in eating quality.

BRIEF DESCRIPTION OF THE DRAWING

The drawing is an illustration by photographic reproduction in color of the foliage and fruit of my new variety, with upper and lower surfaces of the foliage and exterior and a sectional view of the fruit being shown. The colors are as nearly true as reasonably possible in a color representation of this type.

DESCRIPTION OF THE VARIETY

The botanical details of my new and distinct variety of peach tree are based upon observations of specimens grown at Modesto, Calif., with color terminology in accordance with Reinhold Color Atlas by A. Kornerup and J. H. Wanscher.

TREE

Size: Dwarf. Average height 6 to 7 feet.
Vigor: Non-vigorous.
Form: Spreading.

Density: Dense.
Production: Productive.
Bearer: Regular bearer.

TRUNK

Form: Stocky.
Texture: Shaggy.

BRANCHES

Size: Stocky.
Texture: Medium rough.

LEAVES

Size: Medium. Average length 5 inches. Average width 1 inch.
Margin: Crenate.
Thickness: Medium.
Petiole: Medium length. Medium thickness.
Glands: Average number 2. Range 2 to 4 usually positioned on base of leaf blade. Reniform.
Color:
*Upper surface.*—(29-E-5 to 29-E-7).
*Lower surface.*—(30-E-8 to 30-F-8).

FLOWER BUDS

Size: Medium.

FLOWERS

Blooming period: Feb. 25, 1976 to Mar. 11, 1976.
Size: Large, showy.
Color: Pink.
Pollen: Present.

FRUIT

Maturity when described: Eating ripe.
Date of first picking: July 3, 1976.
Date of last picking: July 8, 1976.
Size: Medium to large. Average diameter axially 2½". Average transversely in suture plane 2⅝".
Form: Uniform, symmetrical. Globose to slightly oblate.
Suture: Shallow.
Cavity: Rounded. Average depth 5/16 inches. Average breadth 5/16 inches.
Base: Rounded.
Apex: Pointed.

SKIN

Thickness: Medium.

Texture: Medium.

Tendency to crack: None.

Down: Moderate. Medium length.

Color: Bright yellow undercolor (4-A-8 to 4-B-8). Red blush covering most of the surface of the peach, (7-A-8 to 7-B-8).

FLESH

Texture: Moderately firm.

Ripens: Evenly.

Flavor: Subacid.

Eating quality: Good.

Color: Yellow (4-A-8 to 5-A-6).

STONE

Type: Semi-freestone.

Size: Medium. Average length 1¼". Average breadth 1". Average thickness 13/16".

Tendency to split: Slight.

Color: Light brown (8-C-5).

USE

Home and local market.

KEEPING QUALITY

Medium.

SHIPPING QUALITY

Fair, not firm enough for commercial long distance shipments.

The dwarf peach tree and its fruit may vary slightly due to climatic and soil conditions under which the variety may be grown; the present description being of the variety as grown near Modesto, Calif.

The following is claimed:

1. A new and distinct variety of peach tree as illustrated and described by its dwarf size, having close leaf nodes with attractive foliage, large showy flowers and is further characterized by a productive and regular bearer of medium to large, semi-freestone fruit of good eating quality.

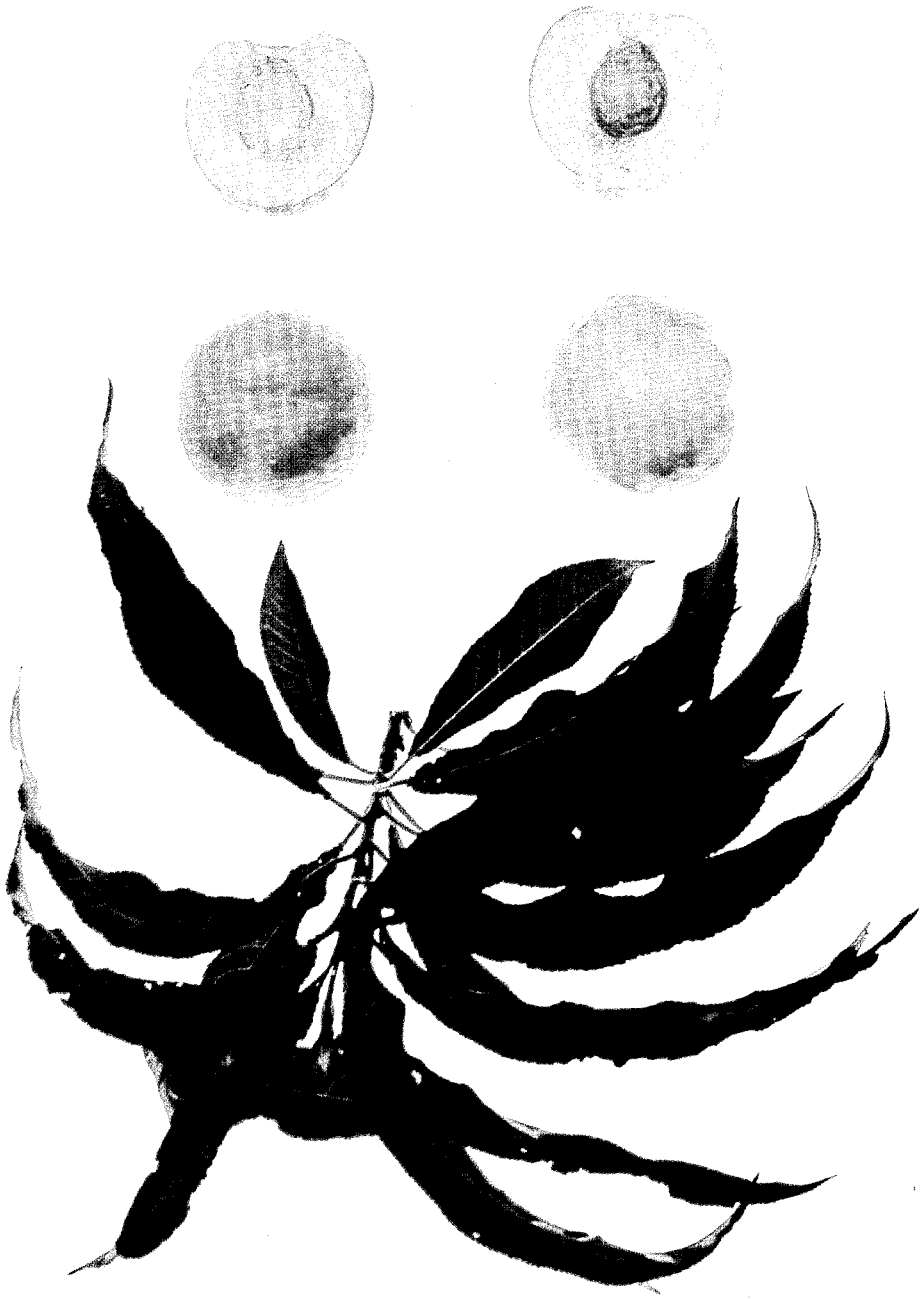

* * * * *